United States Patent
Kim et al.

(10) Patent No.: US 6,617,027 B2
(45) Date of Patent: *Sep. 9, 2003

(54) BIOCOMPATIBLE METALLIC MATERIALS GRAFTED WITH BIOLOGICALLY ACTIVE COMPOUNDS AND PREPARATION THEREOF

(75) Inventors: Young Ha Kim, Seoul (KR); Ki Dong Park, Seoul (KR); Soo Hyun Kim, Seoul (KR); Won Kyu Lee, Daejeon (KR); Hyun Chul Goo, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 09/816,446

(22) Filed: Mar. 26, 2001

(65) Prior Publication Data

US 2001/0037144 A1 Nov. 1, 2001

(30) Foreign Application Priority Data

Mar. 31, 2000 (KR) ......................... 2000-16775

(51) Int. Cl.⁷ ............................................... B32B 27/36
(52) U.S. Cl. ..................................... 428/411.1; 623/1.15
(58) Field of Search ....................... 428/411.1; 427/2.24, 427/2.25, 2.1, 2.3; 606/191, 194, 195, 198; 604/104; 623/1.15

(56) References Cited

U.S. PATENT DOCUMENTS 5,976,169 A * 11/1999 Imran .......................... 606/194
6,440,565 B1 * 8/2002 Kim et al. ................. 428/411.1

* cited by examiner

Primary Examiner—Peter Nerbun
(74) Attorney, Agent, or Firm—Rosenberg, Klein & Lee

(57) ABSTRACT

Disclosed are surface-modified medical metallic materials and preparation thereof. The medical metallic material is prepared by coating a gold or silver thin layer onto a base metal, adsorbing a polyfunctional sulfur compound onto the gold or silver thin layer, and chemically bonding a biologically active material such as heparin or estradiol to the functional group of the sulfur compound. The biologically active material is firmly bonded to the base metal via the sulfur compound. Being significantly improved in anti-thrombogenicity and biocompatibility, the metallic materials are suitable for use in various implants, including stents, artificial cardiac valves and catheters.

27 Claims, 1 Drawing Sheet

Figure 1:
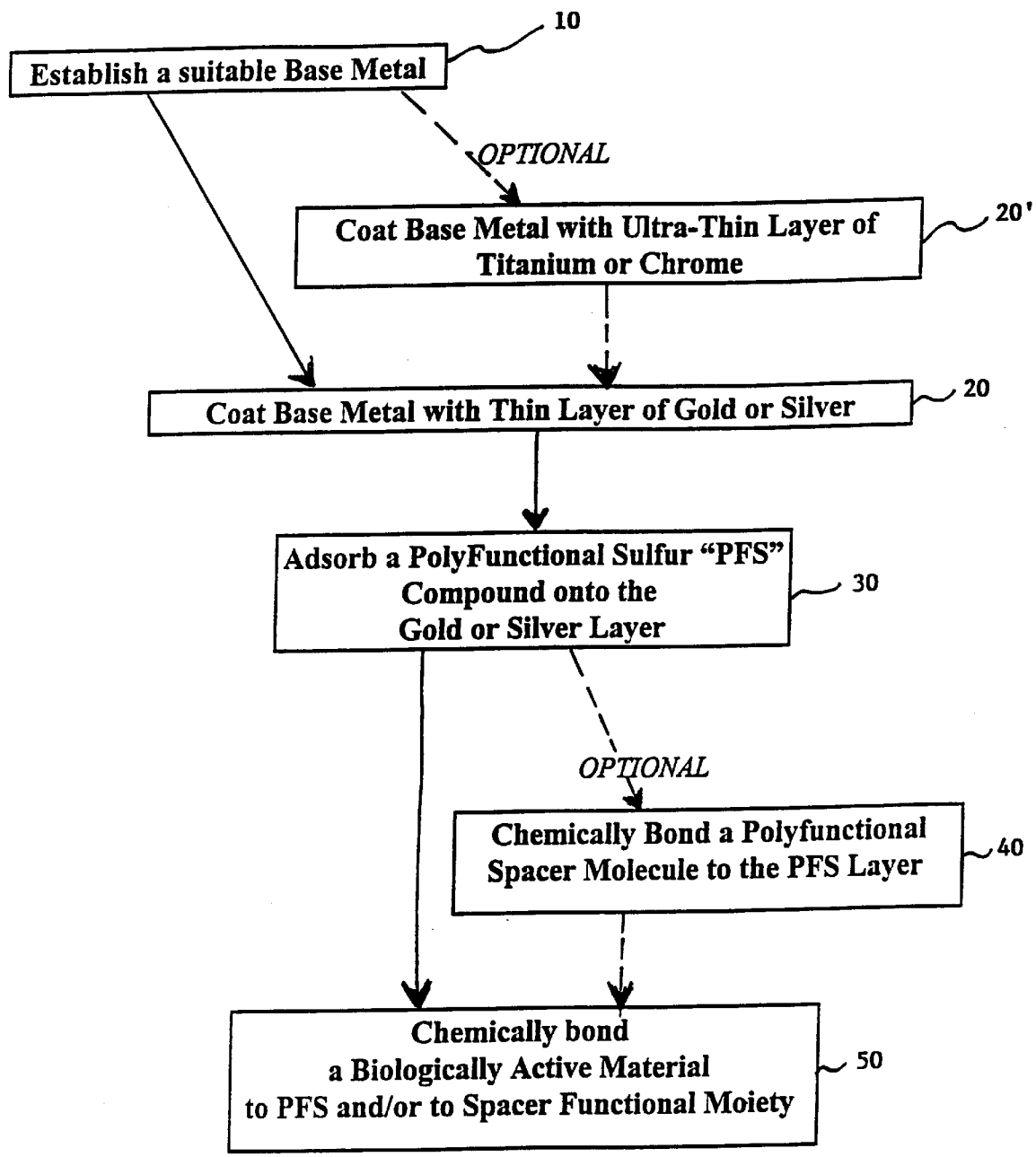

BIOCOMPATIBLE METALLIC MATERIALS GRAFTED WITH BIOLOGICALLY ACTIVE COMPOUNDS AND PREPARATION THEREOF

BACKGROUND OF THE INVENTION

1. Field of the invention

The present invention relates to medical metallic materials, especially medical tools for use in circulatory systems, whose surface is modified to improve antithrombogenicity and biocompatibility. More particularly, the present invention relates to the reliable introduction of a biologically active compound onto the surface of a base metal via a linker, thereby bringing about a great improvement in the antithrombogenicity and biocompatibility of the base metal. Also, the present invention is concerned with a method for preparing such a medical metallic material and with the use of the metallic material in the medical field.

2. Description of the Prior Art

For use in substituting for congenitally or postnatally defective valves of the heart, artificial cardiac valves are generally classified into two groups: valves made of tissues and mechanical valves, which are made of metallic materials. Tissue values show excellent biocompatibility, but poor internal durability due to calcification. On the other hand, mechanical valves endure for extended periods in vivo, but have the disadvantage of forcing the patients to take anticoagulants throughout their lifetime because they are likely to generate thrombus. In spite of extensive research, satisfactory advance has not been yet achieved in the antithrombogenicity of mechanical valves. Indeed, not only is it virtually impossible to prevent thrombogenesis, a normal physiological function of the body, but also its mechanism has not been disclosed completely.

Extensively conducted for the treatment of coronary stenosis is percutaneous transluminal coronary angioplasty in which an intraaortic balloon catheter is inserted within the coronary artery to expand the blood vessel. This operation brings about relatively good results, and development has been and continues to be ongoing in the processes and tools for percutaneous transluminal coronary angioplasty. However, such problems as acute closure and restenosis still remain unsolved.

In order to prevent restenosis, stents, which are spring-like metal grafts, are extensively used. After the operation, stents are inserted within vessels to support vessels. Recently, there has been a tendency toward the expansion of their use. Made of stainless steel, tantalum or titanium-nickel, stents are fabricated into a variety of forms, including balloons and tubes. However, statistics show that restenosis occurs at a rate of 20–30%, on average, even after the implantation of stents. It is found that the failure is attributed mainly to the fact that acute and chronic thrombosis is generated or smooth muscle cells on the inner wall of blood vessels abnormally proliferate owing to injuries formed upon the stent operation.

Because metal surfaces are positively charged in general so that they strongly interact with blood, which contains negative charges, to form thrombus very easily thereon. In addition, the large critical surface tension of metal is described to be another reason for high thrombogenecity (M. F. A. Goosen et al., Biomaterials 17, 685–694, 1996).

A variety of modifications of stents for improvement in antithrombogenicity and biocompatibility are known.

In U.S. Pat. Nos. 5,824,045 yielded to E. Alt and U.S. Pat. No. 5,976,169 yielded to M. A. Imran, gold, platinum, silver or alloys thereof are vapor-deposited onto stents made of stainless steel with the aim of reducing allergic responses and improving antithrombogenicity. The resultant effects were not excellent. A. J. Armini teaches the introduction of beta emission in a stent preventive of restenosis. His U.S. Pat. No. 5,824,045 discloses a coronary stent with a radioactive, radio-opaque coating into which beta-emitting radioisotope ions are implanted. As for the coating, it is formed by vapor-depositing gold, platinum, tantalum or some combination or alloy thereof onto the structural material based on stainless steel, titanium or nickel-titanium alloy.

Because of the absence of chemically active functional groups, metal, unlike organic materials such as polymers, is virtually impossible to chemically modify. Although there are some examples of modification of the surfaces of metal materials, especially, stents, with PEG, polyvinyl alcohol, or other hydrophilic polymers (U.S. Pat. No. 5,843,172 yielded to J. Y. Yan and U.S. Pat. No. 5,897,911 yielded to J. P. Loeffler), the applications are nothing but mere coatings poor in adhesion, so that the antithrombogenicity effects thus obtained are not of a satisfactory level.

Additionally, extensive research has been directed to the coating of polymers onto stents in order to provide antithrombogenicity to the stents. For instance, there have been suggested methods of covering nylon nets (T. Yoshioka, et al., Am. J. Radiol, 15, 673–676, 1988), and coating with silicon (T. Roeren et al., Radiology 174, 1069, 1990) and polyurethane (I. K. De Scheerder et al., J. Am. Coll. Cardiol. 23, 186A, 1994). No satisfactory results were obtained in these studies, either.

Additionally, relevant studies can be found in S. Stheth et al, J. Am. Coll. Cardiol., 23, 187A, 1994, which describes the coating of polymers on medical metal substrates such as stents and catheters; R. S. Schwartz et al., J. Am. Coll. Cardiol., 19, 171A, 1992, which uses fibrin as a coating on stents; and A. M. Lincoff et al., J. Am. Coll. Cardiol., 23, 18A, 1994, in which a medicine-containing polymer is used as a coating on a medical metal substrate to achieve the sustained release of the medicine. These techniques are found to be unable to ensure antithrombogenicity in medical metal substrates.

Heparin, a well known anticoagulant is widely used in the clinic when treating with artificial kidneys or artificial cardiopulmonary machines. Besides antithrombogenicity, heparin was reported to have the function of inhibiting the proliferation of smooth muscle cells (Guyton et al., "Inhibition of rat arterial smooth muscle cell proliferation by heparin", Cir. Res., 46, 625–634, 1980; Cavender et al., "The effects of heparin bonded tantalum stents on thrombosis and neointimal proliferation" Circulation 82, 111–541, 1990). When heparin is bonded to medical metallic substrates, especially stents, they are expected to perform their functions without restenosis by virtue of the heparin's effects, including the prevention of thrombogenesis and the inhibition of the proliferation of smooth muscle cells on vessel walls.

Heparin is a polydispersed, negatively charged polysaccharide synthesized in the body. With a structure of a glycosaminoglycan, heparin has a large amount of sulfonic acid groups and small amounts of carboxylic acid groups, hydroxyl groups and amino groups. Naturally, heparin is synthesized with a molecular weight ranging from 7,000 to 20,000. From this high molecular weight heparin, heparin with a weight of 2,000–5,000 can be prepared. This low molecular weight heparin was reported to be superior in antithrombogenicity to the high molecular weight heparin (R. D. Rosenberg, Heparin: New biomedical and medical aspects, W. De Gruyter, Berlin, 1983). Further, when it is desired, heparin can be degraded by suitable methods such as oxidation (F. Lundberg et al., Biomaterials 19, 1727–1733, 1998).

Medical products in current use, such as catheters, blood tubes, etc., are improved in antithrombogenicity by physically coating or chemically bonding heparin onto substrates (e.g., J. M. Toomasian etc., "Evaluation of Duraflo II heparin coating in prolonged extra-corporeal membrane oxygenation", ASAIO Trans., 34, 410–414, 1988; J. Sanchez etc., "Control of contact activation on end-point immobilized heparin", J. Biomed. Material Res., 29, 655–651, 1995). In many relevant articles and patents, a variety of techniques for coating or bonding heparin are suggested. For instance, before the application of heparin, substrates are first coated with cationic compounds or polymers in order to link negatively charged heparin to the substrates via ionic bonds. Another example is that polymers or hydrogel in which heparin is dispersed or dissolved are coated onto substrates. However, the heparin coated in these techniques is not permanent because it is slowly released into blood or injection solutions. Also, reported are a heparin-containing polymer (U.S. Pat. No. 5,980,972 yielded to N. Ding et al.) and heparin-containing hydrogel (U.S. Pat. No. 5,954,706 yielded to R. A. Sahatjian et al.) for releasing drug in controlled patterns without causing thrombogenesis. The coated heparin of these releasing systems does not show permanent effects, as well, for the same reason as above.

Estradiol derivatives functioning as female hormones, especially 17β-estradiol, are disclosed to inhibit proliferation of the smooth muscle cells in the walls of blood vessels, so that they can be used to effectively restrain restenosis (T. F. Luescher et al., "17β-Estradiol inhibits proliferation and migration of human vascular smooth muscle cells", Cardiovascular Research 32, 980–985, 1996). Since then, the therapy using estradiol and its derivatives has been under study, but there have been yet reported studies in which estradiol or its derivatives are grafted onto metallic materials in order to permanently express the functions thereof.

SUMMARY OF THE INVENTION

Leading to the present invention, intensive and thorough research on the adaptation of metallic materials to biological circumstances, conducted by the present inventors aiming to overcome problems encountered in prior arts, resulted in the finding that biologically active materials, such as heparin and estradiol derivatives, can be grafted onto metallic materials by use of sulfur compounds absorbed in gold or silver layer stably deposited onto the metallic materials, thereby surprisingly improving the metallic materials in antithrombogenicity and biocompatibility. On the surface of a metallic material of the present invention, a gold or silver thin layer is stably coated, to which sulfur compounds are strongly adsorbed, forming charge transfer complexes, and chemically bonded with biologically active materials, such as heparin or estradiol derivatives.

Therefore, it is an object of the present invention to provide a medical metallic material whose surface is modified by coating a gold or silver thin layer onto a base metal by use of a electroplating method, a vacuum vapor deposition method or an ion sputtering method, firmly adsorbing a sulfur compound onto the gold or silver thin layer, and securely grafting a biologically active material such as heparin or an estradiol derivative to the adsorbed sulfur compound, thereby greatly improving the base metal in antithrombogenicity and biocompatibility.

It is another object of the present invention to provide a method for preparing such a medical, metallic material.

It is a further object of the present invention to provide the use of such a medical metallic material in various medical applications, including devices for circulatory systems.

DETAILED DESCRIPTION OF THE INVENTION

In order to clarify the above method,

FIG. 1 depicts a flow diagram for preparing surface-modified medical materials.

As seen in FIG. 1, a base metal is established in flow block 10. The base metal is coated with a thin layer of gold or silver in flow block 20. It is seen that an ultra-thin layer of titanium or chromium may be coated on the base metal in block 20' wherein such coating is optional. The coating as depicted in block 20 then has a polyfunctional sulfur compound adsorbed on the gold or silver layer as shown in flow block 30. Finally, a biologically active material is bonded to the polyfunctional sulfur as shown in block 50. Optionally, a polyfunctional spacer molecule may be chemically bonded to the polyfunctional sulfur compound as depicted in block 40.

Examples of the base metal suitable in the invention include iron, stainless steel, nickel, chrome, copper, titanium, tantalum and alloys thereof, but are not limited thereto.

The gold or silver thin layer formed on the base metal is usually tens of $\mu$m, but may be as thick as hundreds of $\mu$m. Typically, the gold or silver thin layer ranges, in thickness, from 0.1 to 100 $\mu$m.

Optionally, a chrome or titanium ultra-thin layer which has a thickness of 0.01–1 $\mu$m and preferably at a thickness of 0.1–0.5 $\mu$m, may be present between the base metal and the gold or silver thin layer, as taught in U.S. Pat. No. 5,919,126 yielded to A. J. Armini.

By forming charge transfer compounds in cooperation with the gold or silver thin layer, functional sulfur compounds are chemisorbed onto the gold or silver thin layer to afford a self-assembled monolayer. Functional sulfur compounds suitable for use in this purpose can be prepared by bonding functional groups to alkanethiol, dialkylsulfide, dialkyldisulfide, alkylxanthate and/or dialkylthiocarbamate.

In detail, functional sulfur compounds suitable for the present invention are represented by the following chemical formulas 1–8. Compounds of the following chemical formulas 6, 7 and 8 may be used in salt or ester forms.

| | |
|---|---|
| Y-R-SH | 1 |
| Y-R-S-R'-Y | 2 |
| Y-R-S-R' | 3 |
| Y-R-S-S-R'-Y | 4 |
| Y-R-S-S-R' | 5 |
| Y-R-O-CSSH | 6 |
| (Y-R)$_2$-N-CSSH | 7 |
| Y-R-NR'-CSSH | 8 | wherein, Y is a hydroxyl group, an amino group, an isocyanate group, an aldehyde group, a carboxyl group or its acid chloride, acid anhydride or acid amide, an epoxy group, a succineimidyl ester group, a tresilyl group, an oxycarbonylimidazole group, or a nitrophenylcarbonate group; and R and R' are independently an alkyl containing 2–25 carbon atoms.

Examples of the alkanethiol-based functional sulfur compounds represented by the chemical formula 1 include mercaptoethanol, mercaptopropanol, mercaptobutanol, aminoethanethiol, aminomethylpropanethiol, mercaptoacetic acid, mercaptopropionic acid, mercaptosuccinic acid, thiolactic acid, and substituted derivatives thereof, but are not limited thereto.

Examples of the dialkylsulfide-based functional sulfur compounds represented by the chemical formula 2 or 3 include, but not by way of limitation, thiodiethanol, thiodipropanol, methylthioethanol, methylthiopropanol, methylthiobutanol, ethylhydroxyethylsulfide, glucose dimethyl mercaptal, thioethylethylamine, thiodiglycolic acid, thiodipropionic acid, methylthioacetic acid, and substituted derivatives thereof.

Examples of the dialkyldisulfide-based functional sulfur compounds represented by the chemical formula 4 or 5 include hydroxyethyldisulfide, cystamine, dithiopropionic acid, dithiodibutyric acid, and substituted derivatives thereof, which are suggested only for illustrative purposes, but are not to be construed to limit the scope of the present invention.

The functional sulfur compounds chemisorbed onto the gold or silver thin layer are so strong in bonding strength that they are not detached by moderate friction and are stable even in various chemical circumstances, such as weak acid or alkali, and in diluted solvents. Thus, the functional sulfur compounds chemisorbed onto the gold or silver thin layer can be used for medical purposes or applied to the body without causing any deleterious effects.

One of the biologically active materials useful in the present invention is heparin. Heparin contains sulfonic acid groups, carboxylic groups, hydroxyl groups, and amino groups, and aldehyde groups can be introduced through by partial oxidation under suitable conditions (F. Lundberg et al., Biomaterials 19, 1727–1733, 1998). Hence, using the functional group Y of the sulfur compound chemisorbed onto the gold or silver thin layer, heparin can be bonded to the layer under suitable reaction conditions (R. D. Rosenberg, Heparin: New biomedical and medical aspects, W. De. Gruyter, Berlin, 1983).

Meanwhile, the bonded heparin may be deteriorated in activity depending on kinds of the base metal, bonding methods, and reaction conditions. Not only heparin, but also estradiol derivatives may suffer this undesirable phenomenon. It is attributed to the fact that, when general enzymes or biologically active materials are immobilized onto metallic materials, conformational changes and mobility reduction occurs, degrading their biological activity in comparison with their free state. To avoid this problem, a spacer is introduced between the base metal and the grafted biologically active materials such as heparin, in accordance with the present invention.

Another group of the biologically active materials useful in the present invention is composed of estradiol and its derivatives. When these compounds, functioning as female hormones, are not secreted sufficiently as in menopause women, osteoporosis and disorders of circulatory systems are apt to occur.

It is reported that even small quantities of these female hormones are capable of strongly inhibiting the growth and migration of smooth muscle cells in the walls of blood vessels. Concrete examples of these hormones include 17β-estradiol, α-estradiol, estrone, estriol, estradiol benzoate and estradiol cypionate.

Estradiol compounds have two functional groups: alcoholic and phenolic hydroxyl groups. The estradiol derivatives, estradiol benzoate and estradiol cypionate, can be synthesized by linking benzoic acid and cypionic acid to the hydroxyl groups, respectively. It is believed that estradiol compounds cannot be chemically bonded to the functional sulfur compound chemisorbed onto the base metal even if the hydroxyl groups are used. Research results concerning this chemical bond have not yet been reported, nor has evaluation for biological activity of the estradiol compounds grafted onto the base material been.

When account is taken of the action mechanism of estradiol compounds, in which receptors in the walls of blood vessels are involved, they are expected to sufficiently express their biological activity even if grafted onto the base metal. In this regard, the introduction of a spacer, as described above, is helpful in exerting the functions of the biologically active materials.

Therefore, in another aspect of the present invention, there is provided a medical metallic material, comprising a base metal, a gold or silver thin layer coated onto the base metal, a sulfur compound chemisorbed to the gold or silver thin layer, a polyfunctional spacer bonded chemically to the functional group of the sulfur compound, and a biologically active material associated with the polyfunctional spacer.

Suitable as the spacer chemically bonded to the functional group of the sulfur compound are those molecules which have at least two functional groups (Z and Z', where Z and Z' may be identical) so as to bond not only to the functional group (Y) of the sulfur compound chemisorbed onto the gold or silver thin layer, but also the functional group (X) of the heparin, simultaneously. In addition to the difunctionality or polyfunctionality, one of the requirements for the spacer is flexibility. In consideration of polyfunctionality and flexibility, water-soluble polymers of tens to thousands in molecular weight, or alkyl or siloxane polymers with flexible chains are used. Examples of the polyfunctional spacers suitable for use in the present invention include, but not by way of limitation, alkylene glycol, polyalkylene glycol, polyhydric alcohol, polyvinyl alcohol, polyhydroxyalkyl (meth)acrylate, polybasic fatty acids, poly(meth)acrylate, multi-functional polysiloxane, alkylvinylether-maleic anhydride copolymer, multivalent amino compounds, multivalent epoxy compounds, and substituted derivatives thereof.

Also, in a further aspect of the present invention, there is provided a method for preparing metallic materials grafted with biologically active materials, such as heparin or estradiol derivatives, comprising the steps of:

(1) coating a gold or silver thin layer on the surface of a base metal;

(2) chemisorbing a polyfunctional sulfur compound onto the gold or silver thin layer; and (3) chemically bonding the biologically active materials to the functional groups of the sulfur compound.

In the step (1), electroplating, chemical deposition, ion sputtering or thermal vapor deposition may be used for coating the gold or silver thin layer onto the base metal.

When using an electroplating method, the gold or silver thin layer is formed from a gold cyanide or a silver cyanide solution in the presence of an electric field of about 6 volts. This method is advantageous in that gold or silver can be uniformly plated even over substrates having complicated shapes. The thermal deposition is achieved by vaporizing thin layer materials at temperatures near their melting points under ultra-vacuum conditions of $10^{-8}$ mmHg or less to deposit onto substrates. Like thermal deposition, ion sputtering is carried out under ultra-vacuum conditions, but uses electric energy to ionize thin layer materials for deposition. Ion sputtering is extensively applied to the vacuum deposition of gold, silver or aluminum thin layers on base metal, but has difficulty in achieving uniform deposition over substrates of complex shapes. Characterized in that thin layer materials are decomposed and reacted on the surface of substrates to form thin layers, chemical deposition can be conducted at room temperature under low pressures, but is not suitable for the preparation of the medical metallic materials of the present invention.

Although being somewhat different in roughness, stability and wear resistance according to methods employed, the thin layers formed by the above methods are so stable as to endure general friction.

In the step (2), functional sulfur compounds are chemically adsorbed onto the surface of the gold or silver thin layer through the formation of charge transfer complexes, resulting in self-assembled monolayer. Functional sulfur compounds suitable for use in this end, as mentioned previously, can be prepared by grafting alkanediol, dialkylsulfide, dialkyldisulfide, alkylxanthate or dialkyl thiocarbamate with a functional group Y. Required to react with both the functional group X of heparin to be bonded in the step (3) and the hydroxyl group of estradiol derivatives or the functional group Z or Z' of the spacer, the functional group Y may be selected from the group consisting of a hydroxyl group, an amino group, an isocyanate group, an aldehyde group, a carboxyl group or its acid chloride, acid anhydride or acid amide, an epoxy group, a succineimidylester group, a succineimidylcarbonate group, a tresilyl group, an oxycarbonylimidazole group, and a nitrophenylcarbonate group.

Concrete examples of the functional sulfur compounds suitable for use in the present invention include: alkanediol sulfur compounds such as mercaptoethanol, mercaptopropanol, mercaptobutanol, aminoethanethiol, aminomethylpropanethiol, mercaptoacetic acid, mercaptopropionic acid, mercaptosuccinic acid, thiolactic acid, etc.; dialkyl sulfides such as thiodiethanol, thiodipropanol, methylthioethanol, methylthiopropanol, methylthiobutanol, ethylhydroxyethylsulfide, glucose dimethylmercaptal, thioethylethylamine, thiodiglycolic acid, thiodipropionic acid, methylthioacetic acid, etc.; dialkyldisulfides such as cystamine, dithiodipropionic acid, dithiodibutyric acid, etc. Into these compounds, the above-mentioned and other functional groups can be introduced through proper substitution. In fact, neither alkylxanthate sulfur compounds nor dialkylthiocarbamate sulfur compounds are commercially available as derivatives containing appropriate functional group Y. Thus, the necessary derivatives have to be prepared from corresponding starting materials by use of methods known in the art.

These functional sulfur compounds are reported to be attached more easily and stably onto gold than silver (A. Ulman Chem. Rev., 96, 1533–1544, 1996). The chemisorption of the functional sulfur compounds is carried out by immersing a metal specimen at room temperature for 6–24 hours in a diluted solution of the functional sulfur compounds. Suitable for dissolving the sulfur compounds is alcohol. The solution of sulfur compounds has a concentration of 0.5–5 mMol and preferably 1–3 mMol.

In the step (3), a biologically active material such as heparin or an estradiol derivative is bonded directly or preferably through a spacer to the functional sulfur group chemisorbed onto the surface of gold or silver. When the spacer is used, it serves as a linker between the functional group and the biologically active material.

Functional groups X attachable to heparin are summarized in Table 1, below, along with the estradiol derivative's functional groups Y correspondingly bondable thereto. Because estradiol derivatives have endogenous alcoholic and phenolic hydroxyl groups, linking thereto can be achieved in a similar way. The linking between the functional groups X and Y may be conducted by use of well-known methods in the presence of appropriate catalysts.

TABLE 1

| Functional Group of Heparin (X) | Functional Group of Sulfur Compound (Y) |
| --- | --- |
| -Hydroxyl | -Carboxyl and acid chloride, acid anhydride and acid amide<br>-Isocyanate<br>-Aldehyde<br>-Succineimidylester, Succineimidylcarbonate, tresilyl, oxycarbonylimidazole, nitrophenylcarbonate |
| -Amino | -Carboxyl and its derivatives such as acid chloride, acid anhydride, acid amide<br>-Isocyanate<br>-Aldehyde<br>-Epoxy<br>-Succineimidylester, Succineimidylcarbonate, Tresilyl, Oxycarbonylimidazole, Nitrophenylcarbonate |
| -Carboxyl | -Amino,<br>-Acid chloride, Acid anhydride, Acid amide,<br>-Isocyanate<br>-Epoxy |
| -Aldehyde | -Amino<br>-Hydroxyl |
| -Succineimidylester, Succineimidylcarbonate, Tresilyl, Oxycarbonylimidazole, Nitrophenylcarbonate | -Hydroxyl<br>-Amino |

In order to maximize the biological activity of the biologically active material to be bonded, such as heparin or estradiol derivatives, as described above, a spacer may be introduced between the biologically active material and the sulfur compound. Required to be flexible, the spacer may be a hydrophilic polymer with a molecular weight from tens to thousands or an alkyl or siloxane polymer with a flexible chain. Because hydrophilic compounds cause thrombogenesis to a lesser extent when in contact with blood than do hydrophobic compounds, hydrophilic compounds are advantageous as spacers. Also, the spacer has to have at least two functional groups (Z and Z', wherein Z and Z' may be the same or different) such that it can be chemically bonded to both the functional group Y of the sulfur compound and the functional group X of heparin or the estradiol derivative.

Illustrative, but not limitative, examples of these polyfunctional spacers useful in the present invention include alkylene glycol, polyalkylene glycol, polyhydric alcohol, polybasic fatty acid, poly(meth)acrylate, polyfunctional polysiloxane, alkylvinylether-maleic anhydride copolymers, multivalent amino compounds, multivalent epoxy compounds, and substituted derivatives thereof. The linking between the functional group (Z or Z') of the spacer and the functional group Y of the sulfur compound and between the functional group (Z or Z') and the functional group X of the biologically active material such as heparin or an estradiol derivative can be accomplished in the presence of suitable catalysts by methods well known in the art.

In principle, functional sulfur compounds adsorbable to gold or silver thin layers and spacers linkable to the sulfur compounds may be selected from numerous species. Such sulfur compounds and spacers are commercially available or may be prepared from commercially available compounds by use of well-known methods. When they are prepared, it is needed to find out an economically favorable path through which the preparation can be achieved easily and at low costs and for which materials can be readily obtained. Functional groups on the moieties which are to be linked to each other, that is, the functional group X of the biologically active material such as heparin or estradiol derivatives, the functional group Y of the sulfur compound, and/or the functional groups Z and Z' of the spacer, must be so suitably selected as to satisfy the following reaction schemes 1 or 2.

Reaction Scheme 1

Metal/Gold or Silver Thin Layer/Sulfur Compound-R—Y+X-Heparin or Estradiol Derivative→Metal/Gold or Silver Thin Layer/Sulfur Compound-R—Y—X-Heparin or Estradiol Derivative Reaction Scheme 2

Metal/Gold or Silver Thin Layer/Sulfur Compound-R—Y+Z-Spacer-Z'+X-Heparin or Estradiol Derivative→Metal/Gold or Silver Thin Layer/Sulfur Compound-R—Y—Z-Spacer-Z'-X-Heparin or Estradiol Derivative wherein R is an alkyl containing 2–25 carbon atoms.

In order to quantitatively carry out the reactions between the functional groups, suitable catalysts, e.g., catalysts for promoting substitution and addition reactions, such as esterification and amidation, may be employed. Except for special cases, the functional groups are preferably reacted in aqueous solutions and more preferably in aqueous buffers. To achieve optimal conditions for the reaction, pH may be adjusted to acidic or alkaline ranges depending on reaction traits.

The medical metallic materials whose surface is modified according to the present invention is characterized by evaluating the hydrophilicity of the modified surface from the measurement of the angle of contact with the aid of Model CA-DT 11931, Kyowa Interface Sci. Co. Ltd., Japan. In this regard, secondary distilled water is applied to a specimen with a size of 1×3 cm.

Antithrombogenicity is evaluated according to "Method for Measuring Adhesion of Platelets", as will be described, below. A surface-modified metal specimen (a size of 1×1 cm) is put in a disposable syringe, followed by the addition of 2 ml of phosphate buffered saline therein. After the phosphate buffered saline is replaced by 2 ml of platelet-rich plasma ($52 \times 10^4$ platelets/$\mu$l), the syringe is placed for a predetermined time period in a shaking incubator adjusted to 37° C. Then, the syringe is taken from the incubator and the platelets which remain in the plasma are measured with the aid of a Coulter counter or a cytometer to calculate the number of platelets adhering to the specimen (see. H. J. Lee, et al., Polymer (Korea), 21, 1045–1052, 1997).

The chemical composition of the surface of the metallic materials is analyzed by an ATR FT-IR (Attenuated Total reflectance Fourier Transform Infrared) method and an ESCA (electron spectroscopy for chemical analysis) method. ATR FT-IR analysis is conducted with the aid of Brucker FT-IR (IFS 66, Germany) using KRS-5 crystal. Suitable for ESCA is ESCA 2803-S (SSI, U.S.A.) using AlKa x-ray.

Quantification of the heparin introduced to the metallic material can be conducted by a toluidine blue method, a modification of the Smith method (P. K. Smith et al., "Colorimetric method for the assay of heparin content in immobilized heparin preparations", Anal. Biochem., 109, 466–473, 1980). To this end, first, heparin standard solutions ranging, in heparin content, from 0.0001 to 0.0002% by weight are prepared by dissolving appropriate amounts of heparin in 2 ml of each 0.2% NaCl solution. To each of the standard solutions, 3 ml of a toluidine blue solution (25 mg/0.01 N HCl 500 ml) and 3 ml of hexane were added, and stirred for 1 min. After the separation of an aqueous layer from a hexane layer, the aqueous layer is removed and measured for IR absorbance at 631 nm to draw a standard absorption curve. A heparin-grafted metal specimen is immersed in 6 ml of a 0.2% NaCl solution, followed by the addition of 9 ml of the toluidine blue solution and 9 ml of hexane to the NaCl solution. The IR absorbance measured in the same manner is compared with the standard absorption curve to determine the concentration of the heparin introduced.

A better understanding of the present invention may be obtained in light of the following examples which are set forth to illustrate, but are not to be construed to limit the present invention.

In the following examples, the formation of a gold or silver thin layer on base metal was carried out as described in thin layer processes, below.

Thin Film Processes

1. Thermal Deposition Process

After being washed with a chromic acid (Aldrich, U.S.A.)-saturated solution, a metal specimen was installed in a thermal evaporator (Model RH 900, MDC, U.S.A.). The specimen was spaced at a distance of 20 cm from a boat-type molybdenum vaporizing furnace. While the temperature of the furnace was adjusted to about 1,200° C., chrome or titanium was vaporized for 1 hour at a vacuum of $1 \times 10^{-8}$ torr to form a chrome or titanium ultra-thin layer as thin as 200 Å. Subsequently, gold or silver was vaporized for 3 hours to deposit a gold or silver thin layer to a thickness of 20 $\mu$m.

2. Ion Sputtering Process

After being washed with a chromic acid (Aldrich, U.S.A.)-saturated solution, a metal specimen was installed in an ion sputter (IB-3, Eiko Co. Ltd., Japan). While an ion current was flowed at 7 mA, chrome or titanium was vaporized for 40 min at a vacuum of $1 \times 10^{-6}$ torr to coat the metal specimen with a chrome or titanium ultra-thin layer to a thickness of 200 Å. Subsequently, gold or silver was deposited for 3 hours in the same manner to a thickness of about 20 $\mu$m.

3. Electroplating Process

A metal specimen washed with a chromic acid (Aldrich, U.S.A.)-saturated solution was positioned as a cathode in 500 ml of an electrolytic cell which contained gold cyanide or silver cyanide (Aldrich, U.S.A.) at an amount of 15 g/l, potassium cyanide at an amount of 100 g/l, and carbon disulfide at an amount of 0.01 g/l while a platinum sample was used as an anode. Under an electric field of 6 volts applied across the electrodes, the metal specimen was plated for 10 min with gold or silver at a thickness of about 25 $\mu$m.

EXAMPLE 1

After being coated with a gold or silver thin layer and optionally further with a chrome ultra-thin layer in accordance with the thin layer process described above, a stainless steel 316 specimen (Hankuk Synthesis Special Steel Co.

Ltd, Korea) was immersed in 15 ml of a 1 mM 4,4'-dithiobutyric acid solution in ethanol for 12 hours and then washed with copious distilled water. Subsequently, the treated metal specimen was reacted with 15 mg of carbodiimide (Aldrich, U.S.A.) for 24 hours in 15 ml of an aqueous solution (5% w/v) of diaminoPEG (Mw 1,000, Nippon Oil Industrial Co. Ltd., Japan). Afterwards, the metal specimen was transferred to 15 ml of a 5% w/v aqueous solution of heparin (I-A grade, one million units, activity USP 170 units/mg, Sigma, U.S.A.) containing 15 mg of carbodiimide and reacted for 24 hours.

The metal surface was found to have a composition of carbon 66.8%, oxygen 23.7% and sulfur 9.5% on the dithiobutyric acid-adsorbed surface area, a composition of carbon 63.5%, oxygen 31.1% and sulfur 9.5% on the PEG derivative-adopted surface area, and a composition of carbon 65.5%, oxygen 29.6%, sulfur 4.4% and nitrogen 0.5% as measured by ESCA. These ESCA results demonstrated that the reactions had proceeded as desired.

The heparin grafted to the metal specimen was quantified to be 4.85 $\mu g/cm^2$ as measured by the toluidine blue method.

As a result of the measurement for the contact angle of the heparinized stainless steel, it was found that the contact angle was subject to a completely wetted condition, which showed hydrophilicity greater than 56.3° of the un-treated specimen.

Percent platelet adhesion was determined at 60 min after the starting of the platelet adhesion experiment. Platelets adhering to the surface of metal specimens were counted to be 70% less on the surface of the treated stainless steel than on the surface of the non-treated stainless steel. Therefore, the specimen was improved in antithrombogenicity when being treated according to the present invention.

EXAMPLE 2

After being coated with a gold or silver thin layer and optionally further with a titanium ultra-thin layer in accordance with the thin layer process described above, a nickel-titanium alloy specimen (Ni 54%/Ti 46%, NiTi Development Co., U.S.A.) was immersed in 15 ml of a 1 mM cystamine dihydrochloride (Aldrich, U.S.A.) solution in methanol for 6 hours and then washed with copious distilled water. Subsequently, the treated metal specimen was reacted with 15 mg of triethylamine (Aldrich, U.S.A.) for 24 hours in 15 ml of an aqueous solution (5% w/v) of diepoxyPEG (Mw 900, Denacol EX-861, Nagase Chemical, Co. Ltd., Japan). Afterwards, the metal specimen was transferred to 15 ml of a 1% w/v solution of heparin (Mw. ca. 3,000, activity USP 30–50 units/mg, Sigma, U.S.A.) in formamide and reacted for 24 hours.

As in Example 1, carbon was detected on the cystamine-adsorbed surface area as measured by ESCA. FT-IR analysis showed that epoxyPEG was associated. The heparin grafted to the metal specimen was quantified to be 4.24 $\mu g/cm^2$ as measured by the toluidine blue method. The contact angle of the heparinized nickel-titanium alloy was measured to a completely wetted condition, which showed hydrophilicity greater than 68.3° of the un-treated specimen. Percent platelet adhesion was determined at 60 min after the initiation of the platelet adhesion experiment. Platelets adhering to the surface of metal specimens were counted to be about 50% less on the surface of the treated nickel-titanium alloy than on the surface of the non-treated nickel-titanium alloy. Therefore, the specimen was improved in antithrombogenicity when being treated according to the present invention.

EXAMPLE 3

After being coated with a gold or silver thin layer and optionally further with a chrome ultra-thin layer in accordance with the thin layer process described above, a tantalum specimen (Aldrich, U.S.A.) was immersed in 15 ml of a 1 mM thioethylethylamine hydrochloride (Aldrich, U.S.A.) solution in methanol for 6 hours and then washed with copious distilled water. Separately, 10 g of heparin (one million units, activity USP 170 units/mg, Sigma, U.S.A.) was reacted with 1 g of sodium periodate in 200 ml of distilled water for 12 hours in a dark place and added with 10 ml of glycerol. The resulting heparin solution was dialyzed against 10 ml of distilled water and then dried. The heparin thus partially oxidized was found to contain aldehyde (see. F. Lundberg et al., Biomaterials, 19, 1727–1733, 1998). The metal specimen grafted with thioethylethylamine was added in 15 ml of the aqueous oxidized heparin solution (1% w/v) and reacted for 24 hours.

As in Example 1, carbon was detected on the thioethylethylamine-adsorbed surface area as measured by ESCA. The heparin grafted to the metal specimen was quantified to be 2.24 $\mu g/cm^2$ as measured by the toluidine blue method. As a result of the measurement for the angle of contact of the heparinized tantalum specimen, it was found that the contact angle was subject to a completely wetted condition, which showed hydrophilicity greater than 48.5° of the un-treated specimen. Percent platelet adhesion was determined at 60 min after the initiation of the platelet adhesion experiment. Platelets adhering to the surface of metal specimens were counted to be about 40% less on the surface of the treated tantalum specimen than on the surface of the non-treated tantalum specimen. Therefore, the specimen was improved in antithrombogenicity when being treated according to the present invention.

EXAMPLE 4

After being coated with a gold or silver thin layer and optionally further with a titanium ultra-thin layer in accordance with the thin layer process described above, a nickel-titanium specimen was immersed in 15 ml of a 1 mM aminoethanthiol hydrochloride (Aldrich, U.S.A.) solution in ethanol for 12 hours and then washed with copious distilled water. Afterwards, the specimen was placed in 15 ml of an aqueous oxidized solution (1% w/v) of heparin (Mw. ca. 3,000, activity USP 30–50 units/mg, Sigma, U.S.A.) and reacted for 24 hours.

As in Example 1, carbon was detected on the aminoethanthiol-adsorbed surface area as measured by ESCA. The heparin grafted to the metal specimen was quantified to be 3.32 $\mu g/cm^2$ as measured by the toluidine blue method. As a result of the measurement for the contact angle of the heparinized nickel-titanium specimen, it was found that the angle of contact was subject to a completely wetted condition, which showed hydrophilicity greater than 68.3° of the un-treated specimen. Percent platelet adhesion was determined at 60 min after the initiation of the platelet adhesion experiment. Platelets adhering to the surface of metal specimens were counted to be about 55% less on the surface of the treated nickel-titanium specimen than on the surface of the non-treated nickel-titanium specimen. Therefore, the specimen was improved in antithrombogenicity when being treated according to the present invention.

EXAMPLE 5

After being coated with a gold or silver thin layer and optionally further with a chrome ultra-thin layer in accordance with the thin layer process described above, a stainless steel 316 specimen was immersed in 15 ml of a 1 mM cystamine dihydrochloride solution in ethanol for 6 hours and then washed with copious distilled water. Afterwards, the alloy specimen was immersed in 15 ml of an aqueous solution (5% w/v) in dioxycarbonylimidazole PEG (Mw. 1,000, Shearwater Polymers, U.S.A.) and then reacted for 24 hours. Next, the alloy specimen was transferred to 15 ml of an aqueous solution (1% w/v) of heparin (Mw. ca. 3,000, activity USP 30–50 units/mg, Sigma, U.S.A.) and reacted for 24 hours.

Carbon was detected on the cystamine-adsorbed surface area while an PEG compound-adsorbed surface was found to be increased in oxygen composition, as measured by ESCA. These ESCA results demonstrated that the reactions had proceeded as desired. The heparin grafted to the metal specimen was quantified to be 3.47 $\mu g/cm$ as measured by the toluidine blue method. As a result of the measurement for the contact angle of the heparinized stainless steel specimen, it was found that the angle of contact was subject to a completely wetted condition, which showed hydrophilicity greater than 56.3° of the un-treated specimen. Percent platelet adhesion was determined at 60 min after the initiation of the platelet adhesion experiment. Platelets adhering to the surface of metal specimens were counted to be about 62% less on the surface of the treated stainless steel specimen than on the surface of the non-treated stainless steel specimen. Therefore, the specimen was improved in antithrombogenicity when being treated according to the present invention.

EXAMPLE 6

After being coated with a gold or silver thin layer and optionally further with a chrome ultra-thin layer in accordance with the thin layer process described above, a tantalum specimen was immersed in 15 ml of a 1 mM 3-mercapto-1-propanol (Aldrich, U.S.A.) solution in ethanol for 12 hours and then washed with copious distilled water. Subsequently, the treated metal specimen was reacted with 15 mg of carbodiimide for 24 hours in 15 ml of a solution (5% w/v) of a methylvinylether-maleic anhydride copolymer (commercially available from Aldrich, U.S.A. under the brand name of Gantrez, Mw. 80,000). Afterwards, the metal specimen was transferred to 15 ml of a 1% w/v solution of heparin (one million units, activity USP 170 units/mg, Sigma, U.S.A.) in formamide containing 15 mg of carbodiimide and reacted for 24 hours.

Carbon was detected on the cystamine-adsorbed surface area as measured by ESCA. FT-IR analysis showed that the maleic anhydride was associated. These analysis results demonstrated that the reactions had proceeded as desired. The heparin grafted to the metal specimen was quantified to be 2.58 $\mu g/cm^2$ as measured by the toluidine blue method. As a result of the measurement for the contact angle of the heparinized tantalum specimen, it was found that the angle of contact was subject to a completely wetted condition, which showed hydrophilicity greater than 48.5° of the untreated specimen. Percent platelet adhesion was determined at 60 min after the initiation of the platelet adhesion experiment. Platelets adhering to the surface of metal specimens were counted to be about 63% less on the surface of the treated tantalum specimen than on the surface of the non-treated tantalum specimen. Therefore, the specimen was improved in antithrombogenicity when being treated according to the present invention.

EXAMPLE 7

After being coated with a gold or silver thin layer and optionally further with a chrome ultra-thin layer in accordance with the thin layer process described above, a stainless steel specimen was immersed in 15 ml of a 1 mM 3-mercapto-1-propanol (Aldrich, U.S.A.) solution in ethanol for 12 hours and then washed with copious distilled water. Subsequently, the treated metal specimen was reacted with 15 mg of carbodiimide for 24 hours in 15 ml of a solution (5% w/v) of a methylvinylether-maleic anhydride copolymer (commercially available from Aldrich, U.S.A. under the brand name of Gantrez, Mw. 310,000). Afterwards, the metal specimen was transferred to 15 ml of a 1% w/v solution of estradiol (Sigma, U.S.A.) in ethanol containing 15 mg of carbodiimide and reacted for 24 hours.

Carbon was detected on the cystamine-adsorbed surface area as measured by ESCA. FT-IR analysis showed that the maleic anhydride was associated. These analysis results demonstrated that the reactions had proceeded as desired. As a result of the measurement for the angle of contact of the estradiol-treated tantalum specimen, it was found that the contact angle was subject to a completely wetted condition, which showed hydrophilicity greater than 56.3° of the un-treated specimen. Percent platelet adhesion was determined at 60 min after the initiation of the platelet adhesion experiment. Platelets adhering to the surface of metal specimens were counted to be about 45% less on the surface of the treated stainless steel specimen than on the surface of the non-treated stainless steel specimen. Therefore, the specimen was improved in antithrombogenicity when being treated according to the present invention.

As described hereinbefore, biologically active materials such as heparin and estradiol derivatives can be firmly bonded to metallic materials via a linker. A sulfur compound is suitable as the linker and requires a gold or silver coating on the metallic materials for its attachment onto the metal body. Being significantly improved in antithrombogenicity and biocompatibility, the metallic materials are suitable for use in various implants, including stents, artificial cardiac valves and catheters.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A surface-modified, medical metallic material, comprising:
    a base metal;
    a gold or silver thin layer coated on the base metal;
    a functional sulfur compound adsorbed onto the thin layer; and
    a biologically active material bonded chemically to the functional sulfur compound.

2. The surface-modified, medical metallic material as set forth in claim 1, wherein the biologically active material is natural, high-molecular weight heparin with a molecular weight of 7,000–20,000 or low-molecular weight heparin with a molecular weight of 2,000–5,000 derived from the high-molecular weight heparin.

3. The surface-modified, medical metallic material as set forth in claim 2, wherein the biologically active material is the heparin modified by partially oxidizing the natural heparin.

4. The surface-modified, medical metallic material as set forth in claim 1, wherein the biologically active material is selected from the group consisting of 17β-estradiol, α-estradiol, estrone, estriol, estradiol benzoate, and estradiol cypionate.

5. The surface-modified, medical metallic material as set forth in claim 1, wherein the sulfur compound is represented by the following chemical formula 1:

Y—R—SH    1 wherein Y is a hydroxyl group, an amino group, an isocyanate group, an aldehyde group, a carboxyl group or its acid chloride, acid anhydride or acid amide, an epoxy group, a succineimidylester group, a succineimidylcarbonate group, a tresilyl group, an oxycarbonylimidazole group, or a nitrophenylcarbonate group; and R is an alkyl containing 2–25 carbon atoms.

6. The surface-modified, medical metallic material as set forth in claim 1, wherein the sulfur compound is represented by the following chemical formula 2 or 3:

Y—R—S—R'—Y    2
Y—R—S—R'    3 wherein Ys are independently a hydroxyl group, an amino group, an isocyanate group, an aldehyde group, a carboxyl group or its acid chloride, acid anhydride or acid amide, an epoxy group, a succineimidylester group, a succineimidylcarbonate group, a tresilyl group, an oxycarbonylimidazole group, or a nitrophenylcarbonate group; and R and R' are independently an alkyl containing 2–25 carbon atoms.

7. The surface-modified, medical metallic material as set forth in claim 1, wherein the sulfur compound is represented by the following chemical formula 4 or 5:

Y—R—S—S—R'—Y    4
Y—R—S—S—R'    5 wherein Ys are independently a hydroxyl group, an amino group, an isocyanate group, an aldehyde group, a carboxyl group or its acid chloride, acid anhydride or acid amide, an epoxy group, a succineimidylester group, a succineimidylcarbonate group, a tresilyl group, an oxycarbonylimidazole group, or a nitrophenylcarbonate group; and R and R' are independently an alkyl containing 2–25 carbon atoms.

8. The surface-modified, medical metallic material as set forth in claim 1, wherein the sulfur compound is a compound represented by the following chemical formula 6 or a salt or ester thereof:

Y—R—O—CSSH    6 wherein Y is a hydroxyl group, an amino group, an isocyanate group, an aldehyde group, a carboxyl group or its acid chloride, acid anhydride or acid amide, an epoxy group, a succineimidylester group, a succineimidylcarbonate group, a tresilyl group, an oxycarbonylimidazole group, or a nitrophenylcarbonate group; and R is independently an alkyl containing 2–25 carbon atoms.

9. The surface-modified medical metallic material as set forth in claim 1, wherein the sulfur compound is a compound represented by the following chemical formula 7 or 8, or a salt or ester thereof:

(Y—R)$_2$—N—CSSH    7
Y—R—NR'—CSSH    8 wherein Y is a hydroxyl group, an amino group, an isocyanate group, an aldehyde group, a carboxyl group or its acid chloride, acid anhydride or acid amide, an epoxy group, a succineimidylester group, a succineimidylcarbonate group, a tresilyl group, an oxycarbonylimidazole group, or a nitrophenylcarbonate group; and R and R' are independently an alkyl containing 2–25 carbon atoms.

10. The surface-modified, medical metallic material as set forth in claim 5, wherein the sulfur compound of the chemical formula 1 is selected from the group consisting of mercaptoethanol, mercaptopropanol, mercaptobutanol, aminoethanethiol, aminomethylpropanethiol, mercaptoacetic acid, mercaptopropionic acid, mercaptosuccinic acid, thiolactic acid, and substituted derivatives thereof.

11. The surface-modified, medical metallic material as set forth in claim 6, wherein the sulfur compound of the chemical formula 2 or 3 is selected from the group consisting of thiodiethanol, thiodipropanol, methylthioethanol, methylthiopropanol, methylthiobutanol, ethylhydroxyethylsulfide, glucose dimethyl mercaptal, thioethylethylamine, thiodiglycolic acid, thiodipropionic acid, methylthioacetic acid, and substituted derivatives thereof.

12. The surface-modified, medical metallic material as set forth in claim 7, wherein the sulfur compound of the chemical formula 4 or 5 is selected from the group consisting of hydroxyethyldisulfide, cystamine, dithiopropionic acid, dithiodibutyric acid, and substituted derivatives thereof.

13. The surface-modified, medical metallic material as set forth in claim 1, wherein the base metal is selected from the group consisting of stainless steel, titanium, nickel, chrome, copper, tantalum, and alloys thereof.

14. The surface-modified, medical metallic material as set forth in claim 1, wherein the gold or silver thin layer ranges, in thickness, from 0.1 to 100 μm.

15. The surface-modified, medical metallic material as set forth in claim 1, further comprising as a spacer a polyfunctional compound or polymer of tens to thousands in molecular weight between the polyfunctional sulfur compound and the biologically active material.

16. The surface-modified, medical metallic material as set forth in claim 15, wherein the spacer is selected from alkylene glycol, polyalkylene glycol, polyhydric alcohol, polyvinyl alcohol, polyhydroxyalkyl (meth)acrylate, polybasic fatty acids, poly(meth)acrylate, multi-functional polysiloxane, alkylvinylether-maleic anhydride copolymer, polyvalent amino compounds, polyvalent epoxy compounds, and substituted derivatives thereof.

17. The surface-modified, medical metallic material as set forth in claim 15, wherein the spacer is a polyfunctional polyethylene glycol derivative ranging, in molecular weight, from 80 to 10,000.

18. The surface-modified, medical metallic material as set forth in claim 15, wherein the spacer is a polyfunctional alkylvinylether-maleic anhydride copolymer ranging, in molecular weight, from 3,000 to 1,200,000.

19. A method for preparing surface-modified medical metallic materials, comprising the steps of:

coating a gold or silver thin layer onto a base metal;

adsorbing a polyfunctional sulfur compound onto the gold or silver thin layer; and chemically bonding a biologically active material to the functional group of the sulfur compound.

20. The method as set forth in claim 19, wherein the coating step is carried out by use of an electroplating method, a thermal deposition method or an ion sputtering method.

21. The method as set forth in claim 19, further comprising the step of coating a chrome or titanium ultra-thin layer to a thickness of 0.01–1 μm on the surface of the base metal, prior to the coating step.

22. The method as set forth in claim 19, further comprising the step of grafting a polyfunctional compound or polymer of tens to thousands in molecular weight, as a spacer, to the polyfunctional sulfur compound, prior to the bonding step.

23. The method as set forth in claim 19, wherein the bonding step is carried out in the presence of a catalyst for esterification, amidation, substitution or addition reaction to bond the biologically active material to the polyfunctional sulfur compound (or a polymeric spacer).

24. The method as set forth in claim 19, wherein the bonding step is carried out in the presence of a catalyst for esterification, amidation, substitution or addition reaction to bond the biologically active material to the polymeric spacer.

25. The surface-modified metallic material as defined in claim 1 as incorporated into a stent.

26. The surface-modified metallic material as defined in claim 1 as incorporated into a cardiac valve prosthesis.

27. The surface-modified metallic material as defined in claim 1 as incorporated into a catheter.

* * * * *